US010519082B2

(12) United States Patent
Bjorkman et al.

(10) Patent No.: US 10,519,082 B2
(45) Date of Patent: Dec. 31, 2019

(54) REMOVAL OF FEED TREATMENT UNITS IN AROMATICS COMPLEX DESIGNS

(71) Applicant: UOP LLC, Des Plaines, IL (US)

(72) Inventors: Kathryn R. Bjorkman, Oak Park, IL (US); Patrick C. Whitchurch, Sleepy Hollow, IL (US); Rodrigo J. Lobo, Des Plaines, IL (US); Linda S. Cheng, Highland Park, IL (US); Susan A. Somers, Elmhurst, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/825,015

(22) Filed: Nov. 28, 2017

(65) Prior Publication Data

US 2018/0170840 A1 Jun. 21, 2018

Related U.S. Application Data

(60) Provisional application No. 62/436,901, filed on Dec. 20, 2016.

(51) Int. Cl.
*C07C 15/08* (2006.01)
*B01D 3/14* (2006.01)
(Continued)

(52) U.S. Cl.
CPC ............ *C07C 15/08* (2013.01); *B01D 3/009* (2013.01); *B01D 3/06* (2013.01); *B01D 3/143* (2013.01); *C07C 5/2708* (2013.01); *C07C 5/387* (2013.01); *C07C 7/13* (2013.01); *C07C 15/04* (2013.01); *C07C 15/06* (2013.01); *C07C 15/073* (2013.01); *C10G 35/04* (2013.01); *C10G 2300/1088* (2013.01); *C10G 2300/1096* (2013.01); *C10G 2400/30* (2013.01); *Y02P 20/127* (2015.11)

(58) Field of Classification Search
None
See application file for complete search history.

(56) References Cited

U.S. PATENT DOCUMENTS 3,700,744 A * 10/1972 Berger .................... C07C 7/005
203/71
5,171,922 A 12/1992 Anderson
(Continued)

FOREIGN PATENT DOCUMENTS

| GB | 1430121 A | 3/1976 |
| WO | 2013051023 A1 | 4/2013 |
| WO | 2014-031281 A1 | 2/2014 |

OTHER PUBLICATIONS

Xu et.al., Alkylation of Aromatics, Progress in Zeolite Science: A China Perspective , p. 145.
(Continued)

*Primary Examiner* — Tam N Nguyen (57) ABSTRACT

Processes and apparatuses for producing para-xylenes are provided. The processes comprises providing a reformate stream comprising aromatic hydrocarbons to a reformate splitter to provide a reformate bottoms stream and a reformate overhead stream. A portion of the reformate bottoms stream is passed to a para-xylene separation unit for separating para-xylene, wherein the portion of the reformate bottoms stream is passed to the para-xyelene separation unit without an intermediate step for removal of olefins.

10 Claims, 2 Drawing Sheets

(51) Int. Cl.
  *B01D 3/06* (2006.01)
  *C07C 15/073* (2006.01)
  *C07C 5/387* (2006.01)
  *C07C 15/06* (2006.01)
  *C10G 35/04* (2006.01)
  *C07C 15/04* (2006.01)
  *C07C 5/27* (2006.01)
  *C07C 7/13* (2006.01)
  *B01D 3/00* (2006.01)

(56) References Cited

U.S. PATENT DOCUMENTS

| | | | |
|---|---|---|---|
| 6,740,788 B1 | 5/2004 | Maher et al. | |
| 7,288,687 B1 | 10/2007 | Frey et al. | |
| 7,304,193 B1* | 12/2007 | Frey | C07C 5/2737 |
| | | | 208/133 |
| 7,812,208 B2 | 10/2010 | Cheng et al. | |
| 7,820,869 B2 | 10/2010 | Priegnitz et al. | |
| 8,198,502 B2* | 6/2012 | Bresler | C07C 7/005 |
| | | | 585/805 |
| 8,241,501 B2 | 8/2012 | Liu et al. | |
| 8,283,274 B2 | 10/2012 | Cheng et al. | |
| 8,481,795 B2 | 7/2013 | Boldingh et al. | |
| 8,609,922 B2* | 12/2013 | Werba | B01D 3/007 |
| | | | 585/478 |
| 8,722,952 B2 | 5/2014 | Garg et al. | |
| 2009/0326308 A1* | 12/2009 | Kulprathipanja | B01J 20/183 |
| | | | 585/820 |
| 2010/0261941 A1 | 10/2010 | Hagemeister et al. | |
| 2013/0158334 A1* | 6/2013 | Corradi | C07C 7/005 |
| | | | 585/822 |
| 2015/0094507 A1* | 4/2015 | Gattupalli | C07C 7/04 |
| | | | 585/470 |
| 2015/0166436 A1 | 6/2015 | Noe et al. | |
| 2015/0336023 A1* | 11/2015 | Dunet | B01D 1/28 |
| | | | 203/26 |
| 2017/0050901 A1* | 2/2017 | Amelse | B01D 3/143 |
| 2017/0349508 A1* | 12/2017 | Montalbano | C07C 5/2775 |
| 2018/0093932 A1* | 4/2018 | Pednekar | B01D 3/141 |
| 2018/0170834 A1* | 6/2018 | Bjorkman | B01D 3/143 |
| 2018/0186710 A1* | 7/2018 | Abudawoud | C07C 6/123 |
| 2018/0319724 A1* | 11/2018 | Corradi | C07C 5/27 |

OTHER PUBLICATIONS

Hydrocarbon Processing, Petrochemical Processes 2001, CDTECH, a partnership between ABB Lummus Global, and Chemical Research & Licensing. Relevant text (p. 35) Yields: 100,000 tons of cumene.
Kajdas, Major Pathways for used oil disposal and recycling. Part 2, Waste oil re-refining'. Hydrocarbon processing, Sep. 1980, p. 143.
PCT Search Report dated Jun. 10, 2018 for corresponding PCT Application No. PCT/US2018/019824.
U.S. Appl. No. 15/846,331, filed Dec. 19, 2017.

* cited by examiner

REMOVAL OF FEED TREATMENT UNITS IN AROMATICS COMPLEX DESIGNS

CROSS-REFERENCE TO RELATED APPLICATION

This application claims priority from Provisional Application No. 62/436,901 filed Dec. 20, 2016, the contents of which cited application are hereby incorporated by reference in its entirety.

TECHNICAL FIELD

The technical field generally relates to apparatuses and processes for producing xylene isomers in an aromatics complex. More particularly, the present disclosure relates to removal of olefin removal units in an aromatics complex producing para-xylene.

BACKGROUND

Most new aromatics complexes are designed to maximize the yield of benzene and $C_8$ aromatic isomer (para-xylene, meta-xylene, ethylbenzene and ortho-xylene). Para-xylene, meta-xylene and ortho-xylene, are important intermediates which find wide and varied application in chemical syntheses. Para-xylene upon oxidation yields terephthalic acid which is used in the manufacture of synthetic textile fibers and resins. Meta-xylene is used in the manufacture of plasticizers, azo dyes, wood preservers, etc. Ortho-xylene is feedstock for phthalic anhydride production. The distribution of xylene isomers from catalytic reforming and other sources generally does not match that of the sought isomers for chemical intermediates and thus the producer converts the feedstocks to generate more of the sought isomers in the aromatics complexes.

The production of xylenes is practiced commercially in large-scale facilities and is highly competitive. Concerns exist not only about the effective conversion of feedstock through one or more of isomerization, transalkylation and disproportionation to product xylenes, but also other competitive aspects with respect to such facilities including capital costs and energy costs.

A prior art aromatics complex flow scheme has been disclosed by Meyers in the Handbook of Petroleum Refining Processes, 2d. Edition in 1997 by McGraw-Hill.

Various sources have been proposed for monocyclic aromatics as a feed to a xylene production facility. The most prevalent are the catalytic reforming of naphtha fractions and pyrolysis followed by hydrotreating of naphtha fractions. These processes typically produce a wide spectrum of chemical compounds including not only the sought monocyclic aromatics but also polycyclic aromatics and olefins. Polycyclic aromatics and olefins are typically undesirable impurities in xylene production facilities. They can have a negative impact on the product quality and the efficiency of the processes such as by requiring additional process steps, reducing catalyst life, decreasing stability of the product, and causing undesirable product color. Polycyclic aromatics are typically removed by distillation from the desired monocyclic aromatics. These removed polycyclic aromatics are then disposed of in any suitable manner, usually as a fuel, and thus have lesser value. It is also known that the polycyclic aromatics can be converted to useful monocyclic aromatics such as toluene, xylenes and $C_{9+}$ monocyclic aromatics.

The quality of feed streams to the various process units within a xylene production facility is also specified to ensure proper performance. For example, the olefin content of streams fed to some process units of aromatics complex, including the para-xylene separation unit, is limited. Thus, olefin are recognized as a contaminant in the feed to the adsorbent present in the para-xylene separation unit and the conventional practice is to reduce the olefin content to an acceptable level (feed specification limit) using various olefin removal processes such as hydrotreating, hydrogenation, treating with clay and/or molecular sieves and olefin reduction process (ORP). Olefins are for example commonly removed from the xylene production facility feedstock and/or intermediate streams at various locations within the facility by clay treating. In clay treaters, olefins are converted to oligomers which can cause fouling of the clay. The cost to operate clay treaters, including reloading them with fresh clay and disposal of the organic contaminated spent clay, can be a significant financial burden on the commercial-scale producer of xylenes. Moreover, clay treaters can result in alkylation of an olefin to an aromatic ring. Hence, the effluent from a clay treater can contain aromatic rings having $C_{2+}$ substituents such as ethylbenzene, propylbenzene, and methylethylbenzene. Thus the value of the aromatic feedstock for the production of benzene, toluene and xylene is reduced.

Accordingly, it is desirable to provide an improved and cost-effective process and apparatus for production of xylene isomers. Furthermore, other desirable features and characteristics of the present subject matter will become apparent from the subsequent detailed description of the subject matter and the appended claims, taken in conjunction with the accompanying drawings and this background of the subject matter.

BRIEF SUMMARY

Various embodiments contemplated herein relate to apparatuses and processes for producing xylene isomers in an aromatics complex. The exemplary embodiments taught herein illustrate removal of olefin removal units between one or more process units present in an aromatics complex producing para-xylenes In accordance with another exemplary embodiment, a process is provided for the production of para-xylene comprising introducing a raffinate product stream comprising $C_8$ aromatic isomers to an isomerization unit to provide an isomerization effluent, wherein the isomerization effluent is produced in the presence of an ethylbenzene (EB) isomerization catalyst. A portion of the isomerization effluent is passed to a para-xylene separation unit for separating para-xylene, wherein the portion is contacted with an adsorbent under adsorption conditions to provide a xylene extract stream comprising para-xylene and the raffinate product stream, wherein the portion of the isomerization effluent is passed to the para-xyelene separation unit without an intermediate step for removal of olefins.

In accordance with another exemplary embodiment, a process is provided for the production of para-xylene comprising providing a reformate stream comprising aromatic hydrocarbons to a reformate splitter to provide a reformate bottoms stream comprising $C_{7+}$ aromatic hydrocarbons and a reformate overhead stream comprising $C_{7-}$ aromatic hydrocarbons. A portion of the reformate bottoms stream is passed to a para-xylene separation unit for separating para-xylene, wherein the portion is contacted with an adsorbent under adsorption conditions to provide a xylene extract stream comprising para-xylene and a raffinate product stream, wherein the portion of the reformate bottoms stream is passed to the para-xyelene separation unit without an intermediate step for removal of olefins.

In accordance with yet another exemplary embodiment, a process is provided for the production of para-xylene comprising introducing a raffinate product stream comprising $C_8$ aromatic isomers to an isomerization unit to provide an isomerization effluent, wherein the isomerization effluent is produced in the presence of an ethylbenzene (EB) isomerization catalyst. A reformate stream comprising aromatic hydrocarbons is passed to a reformate splitter to provide a reformate bottoms stream comprising $C_{7+}$ aromatic hydrocarbons and a reformate overhead stream comprising $C_{7-}$ aromatic hydrocarbons. A portion of the isomerization effluent and a portion of the reformate bottoms stream is passed to a para-xylene separation unit, wherein the isomerate effluent portion and the reformate bottom portion are contacted with an adsorbent to provide a xylene extract stream comprising para-xylene and the raffinate product stream, wherein the portion of the isomerization effluent and the portion of the reformate bottoms stream are passed to the para-xyelene separation unit without an intermediate step for removal of olefins.

These and other features, aspects, and advantages of the present disclosure will become better understood upon consideration of the following detailed description, drawings and appended claims.

BRIEF DESCRIPTION OF THE DRAWINGS

The various embodiments will hereinafter be described in conjunction with the following FIGURES, wherein like numerals denote like elements.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

DEFINITIONS

As used herein, the term "stream" can include various hydrocarbon molecules and other substances.

As used herein, the term "stream", "feed", "product", "part" or "portion" can include various hydrocarbon molecules, such as straight-chain and branched alkanes, naphthenes, alkenes, alkadienes, and alkynes, and optionally other substances, such as gases, e.g., hydrogen, or impurities, such as heavy metals, and sulfur and nitrogen compounds. Each of the above may also include aromatic and non-aromatic hydrocarbons.

As used herein, the term "overhead stream" can mean a stream withdrawn at or near a top of a vessel, such as a column.

As used herein, the term "bottoms stream" can mean a stream withdrawn at or near a bottom of a vessel, such as a column.

Hydrocarbon molecules may be abbreviated $C_1$, $C_2$, $C_3$, Cn where "n" represents the number of carbon atoms in the one or more hydrocarbon molecules or the abbreviation may be used as an adjective for, e.g., non-aromatics or compounds. Similarly, aromatic compounds may be abbreviated $A_6$, $A_7$, $A_8$, An where "n" represents the number of carbon atoms in the one or more aromatic molecules. Furthermore, a superscript "+" or "−" may be used with an abbreviated one or more hydrocarbons notation, e.g., $C_{3+}$ or $C_{3-}$, which is inclusive of the abbreviated one or more hydrocarbons. As an example, the abbreviation "$C_{3+}$" means one or more hydrocarbon molecules of three or more carbon atoms.

As used herein, the term "zone" or "unit" can refer to an area including one or more equipment items and/or one or more sub-zones. Equipment items can include, but are not limited to, one or more reactors or reactor vessels, separation vessels, distillation towers, heaters, exchangers, pipes, pumps, compressors, and controllers. Additionally, an equipment item, such as a reactor, dryer, or vessel, can further include one or more zones or sub-zones.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top or overhead pressure is the pressure of the overhead vapor at the vapor outlet of the column. The bottom temperature is the liquid bottom outlet temperature. Overhead lines and bottoms lines refer to the net lines from the column downstream of any reflux or reboil to the column unless otherwise shown. Stripping columns omit a reboiler at a bottom of the column and instead provide heating requirements and separation impetus from a fluidized inert media such as steam.

As used herein, the term "rich" can mean an amount of at least generally 50%, and preferably 70%, by mole, of a compound or class of compounds in a stream.

As depicted, process flow lines in the FIGURES can be referred to interchangeably as, e.g., lines, pipes, feeds, gases, products, discharges, parts, portions, or streams.

The term "communication" means that material flow is operatively permitted between enumerated components.

The term "downstream communication" means that at least a portion of material flowing to the subject in downstream communication may operatively flow from the object with which it communicates.

The term "upstream communication" means that at least a portion of the material flowing from the subject in upstream communication may operatively flow to the object with which it communicates.

The term "direct communication" means that flow from the upstream component enters the downstream component without undergoing a compositional change due to physical fractionation or chemical conversion.

The term "predominantly" means a majority, suitably at least 50 mol % and preferably at least 60 mol %.

The term "passing" means that the material passes from a conduit or vessel to an object.

The term "majority" means, suitably at least 40 wt % and preferably at least 50 wt %.

DETAILED DESCRIPTION

The following detailed description is merely exemplary in nature and is not intended to limit the various embodiments or the application and uses thereof. Furthermore, there is no intention to be bound by any theory presented in the preceding background or the following detailed description. Moreover, the reaction conditions including selection of temperature, pressure, LHSV and catalyst in the various units in the aromatics complex described below are conventional which are known to one of ordinary skill in the art, unless wherever mentioned.

Figure 1:
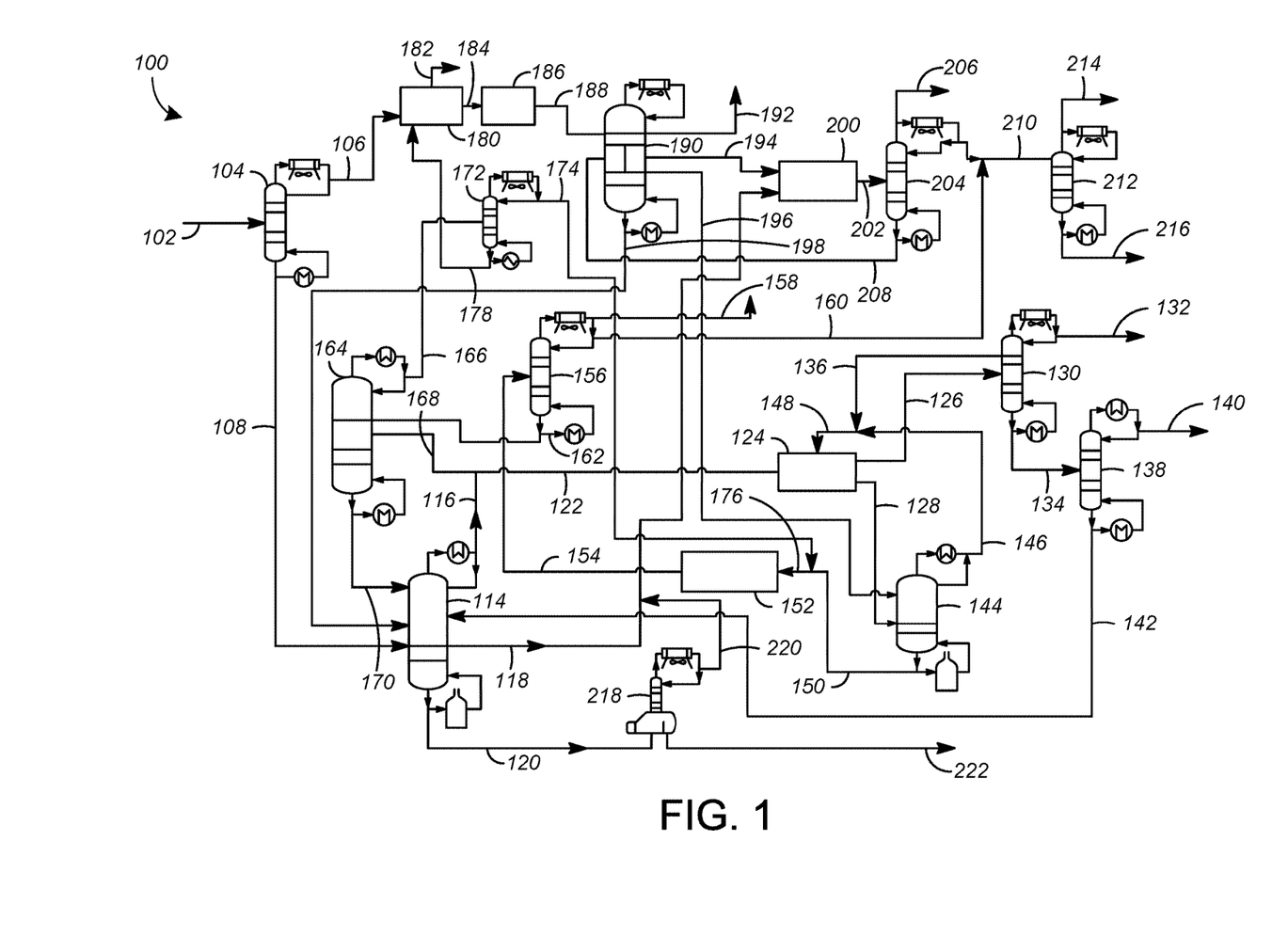
FIG. 1 illustrates an aromatics complex according to an embodiment of the present disclosure.

Various embodiments are directed to apparatuses and processes for producing a $C_8$ aromatic isomer product in an aromatic complex. An exemplary embodiment of the process and apparatus for producing a para-xylene product in an aromatic complex is addressed with reference to a process and apparatus 100 illustrating an aromatics complex according to an embodiment as shown in FIG. 1. The process and apparatus 100 includes a reformate splitter column 104, an aromatics rerun column 114, a para-xylene separation unit 124, an extract column 130, a xylene column 138, a raffinate column 144, an isomerization unit 152, an isomerate stripper column 156, a naphthene splitter column 164, an extractive distillation column 172, an aromatics extraction unit 180, a benzene-toluene (BT) column 190, a transalkylation unit 200, a transalkylation stripper 204, a stabilizer 212 and a heavy aromatics column 218.

In accordance with an exemplary embodiment as shown in FIG. 1, a reformate stream in line 102 comprising aromatic hydrocarbons may be passed to the reformate splitter column 104. A reformate overhead stream in line 106 comprising $C_{7-}$ aromatic hydrocarbons and a reformate bottoms stream in line 108 comprising $C_{7+}$ aromatic hydrocarbons may be withdrawn from the reformate splitter column 104. In accordance with an instant embodiment as shown, an overhead stream from the reformate splitter column 106 may be condensed and separated in a receiver with a portion of the condensed liquid being refluxed back to the reformate splitter column 104 to obtain the reformate overhead stream from a net portion in line 106. Further, as illustrated, the reformate splitter column 104 may include a reboiler at a bottom of the column to vaporize and send a portion of the reformate bottoms stream back to the bottom of the column. A portion of the reformate bottoms stream may be passed to the para-xylene separation unit 124 for separating para-xylene, described in detail later. The portion of the reformate bottoms stream may be passed to the para-xylene separation unit 124 without an intermediate step for removal of olefins. Accordingly, there is no intermediate treatment unit. In accordance with an exemplary embodiment as shown in the FIG. 1, the reformate bottoms stream in line 108 may be passed to the aromatics rerun column 114 for separation. Typically, the reformate bottoms stream in line 108 is passed through an olefin treatment unit to treat residual olefin contaminants before being passed to the aromatics rerun column 114. Examples of the olefin treatment unit include, but are not limited to, a clay treater and an olefin reduction process (ORP) unit. In accordance with an exemplary embodiment as shown in FIG. 1, the reformate bottoms stream in line 108 may be passed directly to the aromatics rerun column 114 without an intermediate step for removal of olefins. Accordingly, the aromatics rerun column 114 may be in direct, downstream communication with the reformate splitter column 104. The aromatics rerun column 114 may further receive a naphthene splitter bottoms stream in line 170 comprising $C_{8+}$ aromatic hydrocarbons and a benzene toluene (hereinafter "BT") column bottoms stream in line 198 comprising xylenes. Further, the aromatics rerun column 114 may receive $C_{8+}$ aromatic hydrocarbons in a bottoms stream in line 142 from the xylene column 138 discussed later. A net overhead rerun column stream in line 116 comprising $C_8$ aromatic isomers and a net bottoms rerun column stream in line 120 rich in $C_9$ and heavier alkylaromatic hydrocarbons may be withdrawn from the aromatics rerun column 114.

In accordance with an exemplary embodiment as shown, the net overhead rerun column stream may be recovered from an overhead of the aromatics rerun column 114 after condensing, flashing and refluxing a portion of the overhead stream from the column. Further, as illustrated, the aromatics rerun column 114 may include a heater at a bottom of the column to vaporize and send a portion of the bottoms stream back to the bottom of the column. A rerun column sidedraw stream in line 118 rich in $C_9$ and $C_{10}$ alkylaromatics may also be withdrawn from the aromatics rerun column 114. In accordance with an exemplary embodiment as shown in FIG. 1, the rerun column sidedraw stream in line 118 may be passed to the transalkylation unit 200.

In accordance with an exemplary embodiment as shown in FIG. 1, the net overhead rerun column stream in line 116 may be combined with a naphthene splitter sidedraw stream in line 168 comprising $C_8$ aromatic isomers to provide a mixed stream in line 122. The mixed stream in line 122 includes para-xylene, meta-xylene, ortho-xylene and ethylbenzene and may be subsequently passed to the para-xylene separation unit 124 to obtain a desired $C_8$ aromatic isomer product via a separation process. The mixed stream line 122 may further include a portion of isomerization effluent from the isomerization unit 152, discussed later in detail. In accordance with an exemplary embodiment as shown in FIG. 1, there is no intermediate olefin treatment step between the aromatic rerun column 114 and para-xylene separation unit 124. In accordance with another exemplary embodiment, there is no intermediate olefin treatment step between the isomerization unit 152 and the para-xylene separation unit 124. In the para-xylene separation unit 124, the mixed stream is contacted with an adsorbent under adsorption conditions. In an embodiment, the adsorption conditions may include an adsorption temperature of less than about 175° C. (350° F.). In accordance with an exemplary embodiment, the adsorbent may be a binderless adsorbent comprising zeolite X having an average crystallite size of less than 1.8 microns. In another aspect, the average crystallite size is from about 500 nanometers to about 1.5 microns. In an aspect, the adsorbent may have at least 95% of its ion-exchangeable sites exchanged with barium or a combination of barium and potassium. In accordance with an exemplary embodiment, the binderless adsorbent may include a converted portion of zeolite X resulting from the conversion of a zeolite X-precursor. Examples of the zeolite X-precursor include, but are not limited to, kaolin clay. Binderless catalysts that can be used in the present disclosure include conventional binderless zeolite catalysts such as those disclosed in U.S. Pat. Nos. 8,283,274, 7,812,208, 7,820,869, and U.S. Pat. Publ. No. 20090326308, the teachings of which are incorporated herein by reference. Applicants have found that such binderless adsorbents are unaffected with respect to capacity and selectivity when subjected to olefins. The Bromine Index of the inlet and outlet of the para-xylene separation unit remains unchanged, indicating that olefins pass through the adsorbent. Accordingly, in various embodiments, a typical olefin treatment unit present between the isomerization unit isomerization unit 152 and the para-xylene separation unit 124 may be removed. In an aspect, a typical olefin treatment unit that is placed downstream of the reformate splitter bottoms may also be removed.

In accordance with the instant embodiment as discussed, the separation process operates, preferably via simulated moving adsorption bed (SMB) employing a desorbent, to provide a para-xylene extract stream in line 126 comprising a mixture of para-xylene and desorbent for the instant embodiment. Examples of desorbent include, and are not limited to toluene and para-diethylbenzene. In accordance with the instant embodiment, toluene is used as the desorbent. The para-xylene extract stream in line 126 may be passed to the extract column 130 which separates para-xylene from the desorbent. A para-xylene stream in line 134 may be withdrawn comprising the desired para-xylenes from the extract column 130. Further, a first return desorbent stream in line 136 is withdrawn which may be subsequently recycled to the para-xylene separation unit 124. In an aspect as shown in FIG. 1, a desorbent drag stream in line 132 may also be withdrawn from the extract column 130. In accordance with an exemplary embodiment, the desorbent drag stream in line 132 may comprise primarily $C_{7-}$ hydrocarbons and may be passed to the BT column 190. In accordance with another exemplary embodiment, the desorbent drag stream in line 132 may be passed to the extractive distillation column 172 to recover additional $C_8$ naphthenes. The para-xylene stream in line 134 may be passed to the para-xylene column 138 to separate the para-xylene product in line 140 from the heavier hydrocarbons obtained as a bottoms stream in line 142 which may be subsequently recycled to the aromatics rerun column 114.

A raffinate stream in line 128 comprising non-equilibrium mixture of $C_8$ aromatics raffinate and the desorbent may be also withdrawn from the para-xylene separation unit 124. The raffinate stream in line 128 may be passed to the raffinate column 144. In accordance with an exemplary embodiment as shown in FIG. 1, a second toluene-enriched stream in line 196 from the BT column 190 may also be introduced to the raffinate column 144 which may act as a makeup for the toluene being used as the desorbent in the para-xylene separation process as per the instant embodiment. The raffinate column 144 separates a raffinate product stream in line 150 for isomerization in isomerization unit 152 from a second return desorbent stream in line 146. In accordance with an exemplary embodiment as shown in FIG. 1, the first desorbent rerun in line 136 and the second desorbent rerun stream in line 146 may combine to provide a combined desorbent rerun stream in line 148 which may be subsequently passed to the para-xylene separation unit 124.

The raffinate product stream in line 150 comprising a non-equilibrium mixture of xylene isomers and ethylbenzene is introduced to the isomerization unit 152 to provide an isomerization effluent in line 154. In accordance with an exemplary embodiment as shown in FIG. 1, a recycle feedstream in line 174 (discussed later) from the extractive distillation column 172 may be recycled to the isomerization unit 152. As shown, the recycle stream in line 174 may combine with the raffinate product stream in line 150 to provide a combined stream in line 176 which may be subsequently passed to the isomerization unit 152. The raffinate product stream is isomerized in reactor 152, which contains an isomerization catalyst to provide a product approaching equilibrium concentrations of $C_8$ aromatic isomers. In accordance with the instant embodiment as discussed for producing para-xylenes, additional para-xylene may be produced by reestablishing an equilibrium or near-equilibrium distribution of xylene isomers. Isomerization catalysts that can be used in the present disclosure include conventional isomerization catalysts such as those disclosed in U.S. Pat. No. 6,740,788, the teachings of which are incorporated herein by reference. In accordance with an exemplary embodiment as discussed, the isomerization catalyst is an ethylbenzene (hereinafter "EB") isomerization catalyst. The isomerization effluent is withdrawn in line 154 from the isomerization unit 152. In the instant aspect as discussed using an ethylbenzene EB isomerization catalyst, the conversion of ethylbenzene to additional xylenes takes place via a $C_8$ naphthene intermediate. Also, toluene may be produced as a byproduct in the isomerization process. Accordingly, the isomerization effluent in 154 may include $C_8$ naphthenes and toluene.

A portion of the isomerization effluent may be passed to the para-xylene separation unit 124 for obtaining para-xylene. The portion of the isomerization effluent may be passed to the para-xylene separation unit 124 without an intermediate step for removal of olefins as discussed above. Accordingly, there is no intermediate treatment unit. In accordance with an exemplary embodiment as shown in FIG. 1, the isomerization effluent in line 154 may be passed to the isomerate stripper column 156. Typically, the isomerization effluent in line 154 is passed through an olefin treatment unit to treat residual olefin contaminants before being passed to the isomerate stripper column 156. Examples of the olefin treatment unit include, but are not limited to, a clary treater and an olefin reduction process (ORP) unit. In accordance with an exemplary embodiment as shown in FIG. 1, the isomerization effluent in line 154 may be passed directly to the isomerate stripper column 156 without an intermediate step for removal of olefins. Accordingly, the isomerate stripper column 156 may be in direct, downstream communication with the isomerization unit 152.

An isomerate stripper overhead stream comprising $C_{6-}$ hydrocarbons in an isomerate overhead line 160 and an isomerate stripper bottoms stream comprising the $C_8$ naphthenes and toluene in isomerate bottoms line 162 is withdrawn from the isomerate stripper column 156, at a first pressure. A vaporous stream in line 158 comprising lighter ends may also be withdrawn from the isomerate stripper column 156 and passed to a vent gas compressor and a stabilizer condenser. The isomerate stripper bottoms stream in isomerate bottoms line 162 may be passed to the naphthene splitter column 164 for further separation. Accordingly, the naphthene splitter column 164 may be in communication with the isomerate bottoms line 162. In an aspect, the naphthene splitter column 164 is in direct, downstream communication with the isomerate bottoms line 162. An overhead naphthene splitter stream in line 166 comprising the $C_8$ naphthenes and toluene is separated from the naphthene splitter bottoms stream in line 170 comprising $C_{8+}$ aromatic hydrocarbons in the naphthene splitter column 164, at a second pressure. In accordance with an exemplary pressure, the second pressure is greater than the first pressure. Accordingly, in an aspect, the naphthene splitter column 164 operates at a higher pressure than the isomerate stripper column 156. Further, the naphthene splitter sidedraw stream in line 168 comprising $C_8$ aromatic isomers is also withdrawn which may be subsequently passed to the xylene separation unit 124 for further processing as discussed above. In accordance with various embodiments, the overhead naphthene splitter stream in line 166 comprises a majority of the $C_8$ naphthenes present in the isomerization effluent and the naphthene splitter sidedraw stream in line 168 comprises majority of the $C_8$ aromatic isomers present in the isomerization effluent.

Subsequently, the overhead naphthene splitter stream in line 166 may be passed to the extractive distillation column 172. Accordingly, the extractive distillation column 172 may be in communication with the naphthene splitter overhead line 166. In an aspect, the extractive distillation column 172 may be in direct, downstream communication with the naphthene splitter overhead line 166. Extractive distillation is a technique for separating mixtures of components having nearly equal volatility and having nearly the same boiling point. In extractive distillation, a solvent is introduced into a main extractive-distillation column above the entry point of the hydrocarbon-containing fluid mixture that is to be separated. The solvent affects the volatility of the hydrocarbon-containing fluid component boiling at a higher temperature differently than the hydrocarbon-containing fluid component boiling at a lower temperature sufficiently to facilitate the separation of the various hydrocarbon-containing fluid components by distillation and such solvent exits with the bottoms fraction. The extractive distillation process in extractive distillation column 172 takes place in the presence of a solvent and separates $C_8$ naphthenes in a recycle feedstream in the recycle line 174 from an extract stream comprising the $C_7$ aromatic hydrocarbons and the solvent withdrawn in an extract line 178. Suitable solvents include tetrahydrothiophene 1,1-dioxide (or sulfolane), NFM (n-formylmorpholine), NMP (n-methylpyrrolidone), diethylene glycol, triethylene glycol, tetraethylene glycol, methoxy triethylene glycol, and mixtures thereof. Other glycol ethers may also be suitable solvents alone or in combination with those listed above. The recycle feedstream in line 174 may be passed to the isomerization unit 152 and processed together with raffinate product stream in line 150 as discussed above. The extract stream in line 178 may be sent to a solvent-recovery column for the separation of the solvent from the $C_7$ aromatic hydrocarbons. In accordance with an exemplary embodiment as shown in FIG. 1, the extract stream is passed to the aromatics extraction unit 180.

Referring back to the reformate splitter column 104, the reformate overhead stream in line 106 comprising $C_{7-}$ aromatic hydrocarbons may be passed to the aromatics extraction unit 180. The aromatics extraction unit 180 can comprise different methods of separating aromatics from a hydrocarbon stream. One industry standard is the Sulfolane™ process, which is an extractive distillation process utilizing sulfolane to facilitate high purity extraction of aromatics. The Sulfolane™ process is well known to those skilled in the art. An aromatics extract stream in line 184 comprising benzene and toluene and a raffinate stream in line 182 comprising non-aromatic hydrocarbons may be withdrawn from the aromatics extraction unit 180. The aromatics extract stream in line 184 may be passed to the BT column 190 to provide benzene and toluene via separation. In accordance with an exemplary embodiment as shown in FIG. 1, the aromatics extract stream in line 184 may be passed through a clay treater 186 to treat residual olefin contaminants and provide a treated aromatics extract stream in line 188 prior to being passed to the BT column 190. A transalkylation bottom stream in line 208 from the transalkylation stripper column 204 may also be passed to the BT column 190. A benzene-enriched stream in line 192, a first toluene-enriched stream in line 194 and the second toluene-enriched stream in line 196 are withdrawn from the BT column 190. Further, the BT column bottoms stream in line 198 is withdrawn and sent to the aromatics rerun column 114 for further processing as discussed above. The second toluene-enriched stream in line 196 may be passed to the raffinate column 144 as also discussed above. The first toluene-enriched stream in line 194 may be passed to the transalkylation unit 200 for production of additional xylenes and benzene.

In accordance with an exemplary embodiment as shown in FIG. 1, in addition to first toluene-enriched stream, the aromatic rerun column sidedraw stream in line 118 rich in $C_9$ and $C_{10}$ alkylaromatics may be passed to the transalkylation unit 200 along with a heavy aromatics column overhead stream in line 220 rich in $C_9$ and $C_{10}$ alkylaromatics from the heavy aromatics column 218. In accordance with an exemplary embodiment as shown in FIG. 1, the aromatic rerun column sidedraw stream in line 118 and the heavy aromatics column overhead stream in line 220 combine to provide a mixed alkylaromatic feedstream in line 224, which may be subsequently provided to the transalkylation unit 200. A make-up hydrogen gas stream (not shown) may also be provided to the transalkylation unit 200. In the transalkylation unit 200, the incoming feedstreams may be contacted with a transalkylation catalyst under transalkylation conditions. In the transalkylation unit 200, the process continues by transalkylating $C_9$ and $C_{10}$ alkylaromatics with toluene. A transalkylated stream in line 202 comprising benzene and xylenes may be withdrawn from the transalkylation unit 200.

Transalkylation catalysts that can be used in the present disclosure include conventional transkylation catalysts such as those disclosed in U.S. Pat. No. 6,740,788, the teachings of which are incorporated herein by reference. Conditions employed in the transalkylation unit 200 normally include a temperature of from about 200° C. to about 540° C. The transalkylation unit 200 is operated at moderately elevated pressures broadly ranging from about 1 kg/cm² to about 60 kg/cm². The transalkylation reaction can be effected over a wide range of space velocities, with higher space velocities affecting a higher ratio of para-xylene at the expense of conversion. Liquid hourly space velocity generally is in the range of from about 0.1 to about 20 $hr^{-1}$.

The transalkylated stream in line 202 may be sent to transalkylation stripper 204 to recover the transalkylation stripper bottoms stream in line 208. Light ends may be removed in transalkylation stripper overhead stream in line 206 and a net overhead stream in line 210 comprising $C_6$ and lighter hydrocarbons may also be withdrawn from the transalkylation stripper 204. Subsequently, the transalkylation stripper bottoms stream in line 208 may be recycled to the BT column 190 to recover benzene product and unconverted toluene for further processing as previously described. The net overhead stream in line 210 may be passed to the stabilizer 212 to provide a stabilizer overhead vaporous stream in line 214 and a stabilizer bottoms stream in line 216. The stabilizer bottoms stream in line 216 may be passed to the aromatics extraction unit 180.

Referring back to the aromatic rerun column 114, net bottoms rerun column stream in line 120 rich in $C_9$ and heavier alkylaromatic hydrocarbons is passed to the heavy aromatics column 218 to separate heavy aromatics comprising $C_{11+}$ alkylaromatic hydrocarbons from $C_9$ and $C_{10}$ alkylaromatics recovered as the heavy aromatics column overhead stream in line 220. The $C_{11+}$ alkylaromatic hydrocarbons may be withdrawn from the heavy aromatics column 218 as a bottoms stream in line 222. The heavy aromatics column overhead stream in line 220 rich in $C_9$ and $C_{10}$ alkylaromatics may be passed to the transalkylation unit 200 for production of additional xylenes and benzene as previously described.

Figure 2:
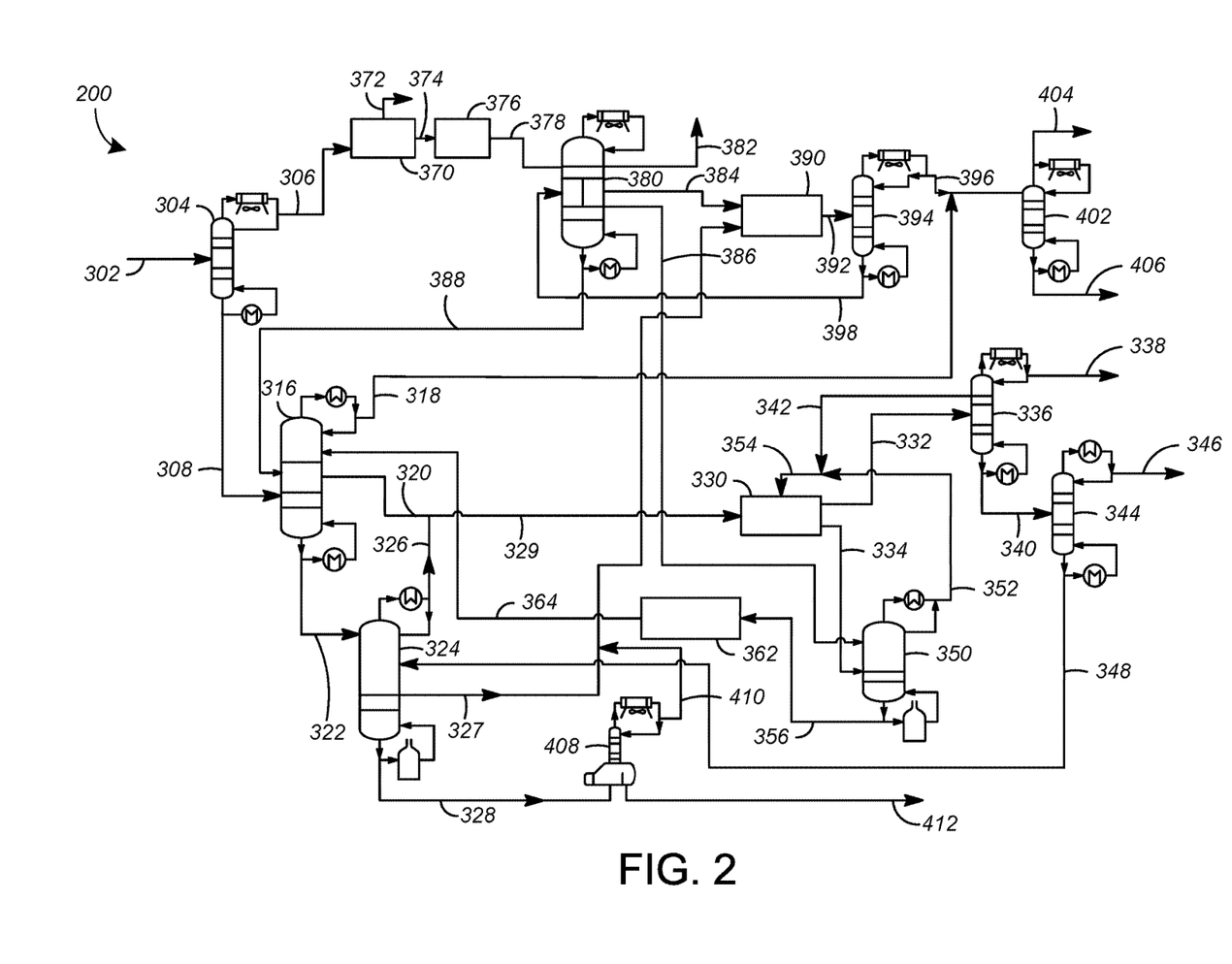
FIG. 2 illustrates an aromatics complex according to another embodiment of the present disclosure.

Turning now to FIG. 2, another embodiment of the aromatics complex is addressed with reference to a process and apparatus 200 providing an alternative scheme for producing a para-xylene product in an aromatic complex is addressed. The process and apparatus 200 includes a reformate splitter column 304, an aromatics stripper column 316, an aromatics rerun column 324, a para-xylene separation unit 330, an extract column 336, a xylene column 344, a raffinate column 350, an isomerization unit 362, an aromatics extraction unit 370, a clay treater 376, a benzene-toluene (BT) column 380, a transalkylation unit 390, a transalkylation stripper 394, a stabilizer 402 and a heavy aromatics column 408.

In accordance with an exemplary embodiment as shown in FIG. 2, a reformate stream in line 302 comprising aromatic hydrocarbons may be introduced to the reformate splitter column 304 to provide a plurality of streams via fractionation. In accordance with an exemplary embodiment as shown in FIG. 2, a reformate overhead stream comprising $C_{7-}$ aromatic hydrocarbons in reformate overhead line 306 and a reformate bottoms stream comprising $C_{7+}$ aromatic hydrocarbons in reformate bottoms line 308 are withdrawn from the reformate splitter column 304. In accordance with an instant embodiment as shown, an overhead stream from the reformate splitter column 304 may be condensed and separated in a receiver with a portion of the condensed liquid being refluxed back to the reformate splitter column 304 to obtain the reformate overhead stream from a net portion in line 306. Further, as illustrated, the reformate splitter column 304 may include a reboiler at a bottom of the column to vaporize and send a portion of the reformate splitter bottoms stream back to the bottom of the column.

A portion of the reformate bottoms stream may be passed to the para-xylene separation unit 330 for separating para-xylene, described in detail later. The portion of the reformate bottoms stream may be passed to the para-xylene separation unit 330 without an intermediate step for removal of olefins. Accordingly, there is no intermediate treatment unit. In accordance with an exemplary embodiment as shown in the FIG. 2, the reformate bottoms in line 308 may be passed to the aromatics stripper column 316 for separation. Typically, the reformate bottoms stream in line 308 is passed through an olefin treatment unit to treat residual olefin contaminants before being passed to the aromatics stripper column 316. Examples of the olefin treatment unit include, but are not limited to, a clay treater and an olefin reduction process (ORP) unit. In accordance with an exemplary embodiment as shown in FIG. 2, the reformate bottoms stream in line 308 may be passed directly to the aromatics stripper column 316 without an intermediate step for removal of olefins. Accordingly, the aromatics stripper column 316 may be in direct, downstream communication with the reformate splitter 304. In accordance with an exemplary embodiment as shown in FIG. 2, an isomerization effluent in line 364 may be passed to the aromatics stripper column 316. Further, in accordance with an exemplary embodiment as shown in FIG. 1, a BT column bottoms stream in line 388 may be passed to the aromatics stripper column 316. The incoming feedstreams undergo separation in the aromatics stripper column 316 and an aromatics stripper overhead stream in line 318 comprising $C_7$ and lighter hydrocarbons, an aromatics stripper sidedraw stream comprising $C_8$ aromatic hydrocarbons in line 320 and an aromatics stripper bottoms stream comprising $C_{8+}$ aromatic hydrocarbons in line 322 are withdrawn from the aromatics stripper column 316. In accordance with an exemplary embodiment, the aromatics stripper column 316 may be a divided wall column.

The aromatics stripper bottoms stream in line 322 may be passed to the aromatics rerun column 324. A xylene column bottoms stream in line 348 may also be passed to the aromatics rerun column 324. An aromatics rerun column overhead stream in line 326, an aromatics rerun column sidedraw stream in line 327 and an aromatic rerun column bottoms stream in line 328 are withdrawn from the aromatics rerun column 324. The aromatics rerun column overhead stream in line 326 is rich in $C_8$ aromatic hydrocarbons and may be combined with the aromatics stripper sidedraw stream in line 320 to provide a mixed stream in line 329.

The mixed stream in line 329 including para-xylene, meta-xylene and ortho-xylene may be passed to the para-xylene separation unit 330 to obtain para-xylene via a separation process. Accordingly, the mixed stream line 329 may include a portion of the reformate bottoms stream. In accordance with an exemplary embodiment as shown in FIG. 2, there is no olefin treatment unit between the reformate splitter column 304 and para-xylene separation unit 330. In the para-xylene separation unit 330, the mixed stream is contacted with an adsorbent under adsorption conditions. In an embodiment, the adsorption conditions may include an adsorption temperature of less than about 175° C. (350° F.). In accordance with an exemplary embodiment, adsorbent may be a binderless adsorbent comprising zeolite X having an average crystallite size of less than 1.8 microns. In another aspect, the average crystallite size is from about 500 nanometers to about 1.5 microns. In an aspect, the adsorbent may have at least 95% of its ion-exchangeable sites exchanged with barium or a combination of barium and potassium. In accordance with an exemplary embodiment, the binderless adsorbent may include a converted portion of zeolite X resulting from the conversion of a zeolite X-precursor. Examples of the zeolite X-precursor include, but are not limited to, kaolin clay. Binderless catalysts that can be used in the present disclosure include conventional binderless zeolite catalysts such as those disclosed in U.S. Pat. Nos. 8,283,274, 7,812,208, 7,820,869, and U.S. Pat. Publ. No. 20090326308, the teachings of which are incorporated herein by reference. Applicants have found that such binderless adsorbents are unaffected with respect to capacity and selectivity when subjected to olefins. The Bromine Index of the inlet and outlet of the para-xylene separation unit remains unchanged, indicating that olefins pass through the adsorbent. Accordingly, in various embodiments, a typical olefin treatment unit present between the reformate splitter column 304 and the para-xylene separation unit 330 may be removed. In an aspect, a typical olefin treatment unit that is placed downstream of the reformate splitter bottoms may also be removed.

In accordance with the instant embodiment as discussed, the para-xylene separation unit 330 operates, preferably via simulated moving adsorption bed (SMB) employing a desorbent, to provide a xylene extract stream in line 332 which is para-xylene extract stream comprising a mixture of para-xylene and desorbent for the instant embodiment. In accordance with various embodiments, the desorbent may be any aromatic hydrocarbon with a lower boiling point than the $C_8$ aromatic isomers. In accordance with the instant embodiment, toluene is used as the desorbent.

The para-xylene extract stream in line 332 may be passed to the extract column 336 which separates para-xylene from the desorbent. A para-xylene stream in line 340 may be withdrawn comprising the desired para-xylenes from the extract column 336. Further, a first return desorbent stream in line 342 is withdrawn which may be subsequently recycled to the para-xylene separation unit 330. In an aspect as shown in FIG. 1, a desorbent drag stream in line 338 may also be withdrawn from the extract column 336. In accordance with an exemplary embodiment, the desorbent drag stream in line 338 may comprise primarily $C_{7-}$ hydrocarbons and may be passed to the BT column 380. The para-xylene stream in line 340 may be passed to the xylene column 344. In accordance with the instant embodiment as discussed, the xylene column is a para-xylene column. The para-xylene column 344 may separate the para-xylene product in line 146 from the heavier hydrocarbons obtained as a bottoms stream in line 348 which may be subsequently recycled to the aromatics rerun column 324 and processed further as previously described. In accordance with an instant embodiment as shown, an overhead stream from the para-xylene column 344 may be condensed and separated with a portion of the condensed liquid being refluxed back to the para-xylene column 346 to obtain the para-xylene product from a net portion in line 346. Further, as illustrated, the para-xylene column 344 may include a reboiler at a bottom of the column to vaporize and send a portion of the bottoms stream back to the bottom of the column. In an aspect, pressure in para-xylene column 344 is approximately about 60 psig. In such an aspect, the condenser of the para-xylene column 344 can be used to reboil the reformate splitter column 104 with the use of high flux tubes. In another aspect, such high flux tubes may be used on the para-xylene column 344 so that high pressure steam can be used as a heat source.

A raffinate stream in line 334 comprising non-equilibrium mixture of $C_8$ aromatics raffinate and the desorbent may be also withdrawn from the para-xylene separation unit 330. The raffinate stream in line 334 may be passed to the raffinate column 350. In accordance with an exemplary embodiment as shown in FIG. 2, a second toluene-enriched stream in line 386 from the BT column 380 may also be introduced to the raffinate column 350 which may act as a makeup for the toluene being used as the desorbent in the para-xylene separation process as per the instant embodiment. The raffinate column 350 separates a raffinate product stream in line 356 for isomerization in isomerization unit 362 from a second return desorbent stream in line 352. In accordance with an exemplary embodiment as shown in FIG. 2, the first desorbent return stream in line 342 and the second desorbent return stream in line 352 may combine to provide a combined desorbent return stream in line 354 which may be subsequently passed to the para-xylene separation unit 330.

In accordance with an exemplary embodiment as shown in FIG. 2, the raffinate product stream is contacted with an isomerization catalyst in the isomerization unit 362 at isomerization conditions to obtain the isomerization effluent in line 364. The isomerization unit 362 comprises isomerization targeted specifically to the isomerization of xylenes in the feedstock to a near-equilibrium mixture with minimal conversion to lighter and heavier products. The isomerization unit 362 may comprise a single reactor or two or more separate reactors with suitable means there between to ensure that the desired isomerization temperature is maintained at the entrance to each reactor. The reactants may be contacted with the catalyst bed in upward-, downward-, or radial-flow fashion. In accordance with an exemplary embodiment as discussed, the isomerization catalyst is an ethylbenzene (hereinafter "EB") dealkylation catalyst.

The isomerization catalyst favorably comprises a zeolitic aluminosilicate selected from those which have a $Si:Al_2$ ratio greater than about 10, preferably greater than 20, and a pore diameter of about 5 to 8 angstroms (Å). Specific examples of suitable zeolites are the MFI, MEL, EUO, FER, MFS, MTT, MTW, TON, MOR and FAU types of zeolites. A particularly favored MFI-type zeolite is gallium-MFI, with gallium as a component of the crystal structure.

As shown in FIG. 2, the isomerization effluent in line 364 withdrawn from the isomerization unit 362 may be passed to the aromatics stripper column 316 and processed further as previously described. Referring back to the reformate splitter column 304, the reformate splitter overhead stream in reformate overhead line 306 comprising $C_{7-}$ aromatic hydrocarbons may be passed to an aromatics-extraction and a fractionation step to provide a benzene product stream and a toluene enriched stream. The reformate overhead stream in reformate overhead line 306 may be passed to the aromatics extraction unit 370. The aromatics extraction unit 370 can comprise different methods of separating aromatics from a hydrocarbon stream. One industry standard is the Sulfolane™ process, which is an extractive distillation process utilizing sulfolane to facilitate high purity extraction of aromatics. The Sulfolane™ process is well known to those skilled in the art. An aromatics extract stream in line 374 comprising benzene and toluene and a raffinate stream in line 372 comprising non-aromatic hydrocarbons may be withdrawn from the aromatics extraction unit 370. The aromatics extract stream in line 374 may be passed to the BT column 380 to provide benzene and toluene via separation. In accordance with an exemplary embodiment as shown in FIG. 2, the aromatics extract stream in line 374 may be passed through a clay treater 376 to treat residual olefin contaminants and provide a treated aromatics extract stream in line 378 prior to being passed to the BT column 380. A transalkylation stripper bottoms stream in line 398 from the transalkylation stripper column 394 may also be passed to the BT column 380. A benzene-enriched stream in line 382, a first toluene-enriched stream in line 384 and the second toluene-enriched stream in line 386 are withdrawn from the BT column 380. Further, the BT column bottoms stream in line 388 is withdrawn and sent to the aromatics stripper column 316 for further processing as previously described. The second toluene-enriched stream in line 386 may be passed to the raffinate column 350. The first toluene-enriched stream in line 384 may be passed to the transalkylation unit 390 for production of additional xylenes and benzene.

In accordance with an exemplary embodiment as shown in FIG. 2, in addition to first toluene-enriched stream, the aromatics rerun column sidedraw stream in line 327 rich in $C_9$ and $C_{10}$ alkylaromatics may be passed to the transalkylation unit 390 along with a heavy aromatics column overhead stream in line 410 rich in $C_9$ and $C_{10}$ alkylaromatics from the heavy aromatics column 408. A make-up hydrogen gas stream (not shown) may also be provided to the transalkylation unit 390. In the transalkylation unit 390, the incoming feedstreams may be contacted with a transalkylation catalyst under transalkylation conditions. In the transalkylation unit 390, the process continues by transalkylating $C_9$ and $C_{10}$ alkylaromatics with toluene. A transalkylated stream in line 392 comprising benzene and xylenes may be withdrawn from the transalkylation unit 390.

Transalkylation catalysts that can be used in the present disclosure include conventional transkylation catalysts such as those disclosed in U.S. Pat. No. 6,740,788, the teachings of which are incorporated herein by reference. Conditions employed in the transalkylation unit 390 normally include a temperature of from about 200° C. to about 540° C. The transalkylation unit 390 is operated at moderately elevated pressures broadly ranging from about 1 kg/cm' to about 60 kg/cm². The transalkylation reaction can be effected over a wide range of space velocities, with higher space velocities affecting a higher ratio of para-xylene at the expense of conversion. Liquid hourly space velocity generally is in the range of from about 0.1 hr$^{-1}$ to about 20 hr$^{-1}$.

The transalkylated stream in line 392 may be sent to transalkylation stripper 394 to recover the transalkylation stripper bottoms stream in line 398. A net overhead stream in line 396 comprising $C_6$ and lighter hydrocarbons may also be withdrawn from the transalkylation stripper 394. Subsequently, the transalkylation stripper bottoms stream in line 398 may be recycled to the BT column 380 to recover benzene product and unconverted toluene for further processing as previously described. The net overhead stream in line 396 along with the aromatics stripper overhead stream in line 318 may be passed to the stabilizer 402 to provide a stabilizer overhead vaporous stream in line 404 and a stabilizer bottoms stream in line 406. In various embodiments, the stabilizer bottoms stream in line 406 may be passed to the aromatics extraction unit 370. In other embodiments, the stabilizer bottoms stream 406 may be passed to the transalkylation stripper 194.

Referring back to the aromatics rerun column 324, the aromatic rerun column bottoms stream in line 328 rich in $C_9$ and heavier alkylaromatic hydrocarbons is passed to the heavy aromatics column 408 to separate heavy aromatics comprising $C_{11+}$ alkylaromatic hydrocarbons from $C_9$ and $C_{10}$ alkylaromatics recovered as the heavy aromatics column overhead stream in line 410. The $C_{11+}$ alkylaromatic hydrocarbons may be withdrawn from the heavy aromatics column 408 as a bottoms stream in line 412. The heavy aromatics column overhead stream in line 410 rich in $C_9$ and $C_{10}$ alkylaromatics may be passed to the transalkylation unit 390 for production of additional xylenes and benzene as previously described.

SPECIFIC EMBODIMENTS

While the following is described in conjunction with specific embodiments, it will be understood that this description is intended to illustrate and not limit the scope of the preceding description and the appended claims.

A first embodiment of the invention is a process for the production of para-xylene, wherein the process comprises a) introducing a raffinate product stream comprising $C_8$ aromatic isomers to an isomerization unit to provide an isomerization effluent, wherein the isomerization effluent is produced in the presence of an ethylbenzene (EB) isomerization catalyst; and b) passing a portion of the isomerization effluent to a para-xylene separation unit for separating para-xylene, wherein the portion is contacted with an adsorbent under adsorption conditions to provide a xylene extract stream comprising para-xylene and the raffinate product stream, wherein the portion of the isomerization effluent is passed to the para-xyelene separation unit without an intermediate step for removal of olefins. An embodiment of the invention is one, any or all of prior embodiments in this paragraph up through the first embodiment in this paragraph further comprising a) passing the isomerization effluent to an isomerate stripper column to provide an isomerate stripper overhead stream comprising $C_{6-}$ hydrocarbons and an isomerate stripper bottoms stream; b) passing the isomerate stripper bottoms stream to a naphthene splitter column to provide an overhead naphthene splitter stream comprising the $C_8$ naphthenes and $C_7$ aromatic hydrocarbons and a naphthene splitter sidedraw stream comprising the portion of the isomerization effluent and a naphthene splitter bottoms stream comprising C8+ aromatic hydrocarbons. An embodiment of the invention is one, any or all of prior embodiments in this paragraph up through the first embodiment in this paragraph further comprising passing the naphthene splitter bottoms stream to an aromatics rerun column to provide a net overhead rerun column stream, wherein the net overhead rerun column stream is mixed with the naphthene splitter sidedraw stream to provide the portion of the isomerization effluent being passed to the para-xylene separation unit. An embodiment of the invention is one, any or all of prior embodiments in this paragraph up through the first embodiment in this paragraph further comprising providing a reformate stream comprising aromatic hydrocarbons to a reformate splitter to provide a reformate bottoms stream comprising $C_{7+}$ aromatic hydrocarbons and a reformate overhead stream comprising $C_{7-}$ aromatic hydrocarbons. An embodiment of the invention is one, any or all of prior embodiments in this paragraph up through the first embodiment in this paragraph further comprising passing a portion of the reformate bottom stream to the para-xylene separation unit without an intermediate step for removal of olefins. An embodiment of the invention is one, any or all of prior embodiments in this paragraph up through the first embodiment in this paragraph, wherein the intermediate step comprises a clay treater. An embodiment of the invention is one, any or all of prior embodiments in this paragraph up through the first embodiment in this paragraph, wherein the intermediate step comprises an olefin reduction process (ORP) unit. An embodiment of the invention is one, any or all of prior embodiments in this paragraph up through the first embodiment in this paragraph, wherein the adsorbent is a binderless adsorbent comprising zeolite X having an average crystallite size of less than 1.8 microns. An embodiment of the invention is one, any or all of prior embodiments in this paragraph up through the first embodiment in this paragraph, wherein the adsorbent has at least 95% of its ion-exchangeable sites exchanged with barium or a combination of barium and potassium. An embodiment of the invention is one, any or all of prior embodiments in this paragraph up through the first embodiment in this paragraph, wherein the para-xylene separation unit is a simulated moving bed adsorption unit. An embodiment of the invention is one, any or all of prior embodiments in this paragraph up through the first embodiment in this paragraph, wherein the para-xylene separation unit uses a desorbent with a lower boiling point than the $C_8$ aromatic isomers.

A second embodiment of the invention is a process for the production of para-xylene, wherein the process comprises a) providing a reformate stream comprising aromatic hydrocarbons to a reformate splitter to provide a reformate bottoms stream comprising $C_{7+}$ aromatic hydrocarbons and a reformate overhead stream comprising $C_{7-}$ aromatic hydrocarbons; and b) passing a portion of the reformate bottoms stream to a para-xylene separation unit for separating para-xylene, wherein the portion is contacted with an adsorbent under adsorption conditions to provide a xylene extract stream comprising para-xylene and a raffinate product stream, wherein the portion of the reformate bottoms stream is passed to the para-xyelene separation unit without an intermediate step for removal of olefins. An embodiment of the invention is one, any or all of prior embodiments in this paragraph up through the second embodiment in this paragraph further comprising passing the reformate bottoms stream to an aromatics rerun column without an intermediate step for removal of olefins. An embodiment of the invention is one, any or all of prior embodiments in this paragraph up through the second embodiment in this paragraph further comprising passing the reformate bottoms stream to an aromatics stripper column without an intermediate step for removal of olefins. An embodiment of the invention is one, any or all of prior embodiments in this paragraph up through the second embodiment in this paragraph, wherein the intermediate step comprises a clay treater. An embodiment of the invention is one, any or all of prior embodiments in this paragraph up through the second embodiment in this paragraph, wherein the intermediate step comprises an olefin reduction process (ORP) unit. An embodiment of the invention is one, any or all of prior embodiments in this paragraph up through the second embodiment in this paragraph, wherein the adsorbent is a binderless adsorbent comprising zeolite X having an average crystallite size of less than 1.8 microns. An embodiment of the invention is one, any or all of prior embodiments in this paragraph up through the second embodiment in this paragraph, wherein the adsorbent has at least 95% of its ion-exchangeable sites exchanged with barium or a combination of barium and potassium.

A third embodiment of the invention is a process for the production of para-xylene, wherein the process comprises a) introducing a raffinate product stream comprising $C_8$ aromatic isomers to an isomerization unit to provide an isomerization effluent, wherein the isomerization effluent is produced in the presence of an ethylbenzene (EB) isomerization catalyst; b) providing a reformate stream comprising aromatic hydrocarbons to a reformate splitter to provide a reformate bottoms stream comprising $C_{7+}$ aromatic hydrocarbons and a reformate overhead stream comprising $C_{7-}$ aromatic hydrocarbons; and c) passing a portion of the isomerization effluent and a portion of the reformate bottoms stream to a para-xylene separation unit, wherein the isomerate effluent portion and the reformate bottom portion are contacted with an adsorbent to provide a xylene extract stream comprising para-xylene and the raffinate product stream, wherein the portion of the isomerization effluent and the portion of the reformate bottoms stream are passed to the para-xyelene separation unit without an intermediate step for removal of olefins. An embodiment of the invention is one, any or all of prior embodiments in this paragraph up through the third embodiment in this paragraph, wherein the intermediate step comprises a clay treater. An embodiment of the invention is one, any or all of prior embodiments in this paragraph up through the third embodiment in this paragraph, wherein the intermediate step comprises an olefin reduction process (ORP) unit. An embodiment of the invention is one, any or all of prior embodiments in this paragraph up through the third embodiment in this paragraph, wherein the adsorbent is a binderless adsorbent comprising zeolite X having an average crystallite size of less than 1.8 microns. An embodiment of the invention is one, any or all of prior embodiments in this paragraph up through the third embodiment in this paragraph, wherein the adsorbent has at least 95% of its ion-exchangeable sites exchanged with barium or a combination of barium and potassium.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for the production of para-xylene, wherein the process comprises:
    a) introducing a raffinate product stream comprising $C_8$ aromatic isomers to an isomerization unit to provide an isomerization effluent, wherein the isomerization effluent is produced in the presence of an ethylbenzene (EB) isomerization catalyst;
    b) passing a portion of the isomerization effluent to a para-xylene separation unit for separating para-xylene, wherein said portion is contacted with an adsorbent under adsorption conditions to provide a xylene extract stream comprising para-xylene and the raffinate product stream; and,
    c) passing the remained portion of the isomerization effluent to the isomerate stripper column to provide an isomerate stripper overhead stream comprising $C_{6-}$ hydrocarbons and an isomerate stripper bottoms stream; and
    d) passing the isomerate stripper bottoms stream to a naphthene splitter column to provide an overhead naphthene splitter stream comprising the $C_8$ naphthenes and $C_7$ aromatic hydrocarbons, a naphthene splitter sidedraw stream comprising the portion of the isomerization effluent that is passed to a para-xylene separation unit, and a naphthene splitter bottoms stream comprising $C_{8+}$ aromatic hydrocarbons,
    wherein the naphthene splitter sidedraw stream is passed to the para-xylene separation unit without an intermediate step for removal of olefins.

2. The process of claim 1 further comprising passing the naphthene splitter bottoms stream to an aromatics rerun column to provide a net overhead rerun column stream, wherein the net overhead rerun column stream is mixed with the naphthene splitter sidedraw stream to provide the portion of the isomerization effluent being passed to the para-xylene separation unit.

3. The process of claim 1 further comprising providing a reformate stream comprising aromatic hydrocarbons to a reformate splitter to provide a reformate bottoms stream comprising $C_{7+}$ aromatic hydrocarbons and a reformate overhead stream comprising $C_{7-}$ aromatic hydrocarbons.

4. The process of claim 3 further comprising passing a portion of the reformate bottom stream to the para-xylene separation unit without an intermediate step for removal of olefins.

5. The process of claim 1, wherein the intermediate step comprises a clay treater.

6. The process of claim 1, wherein the intermediate step comprises an olefin reduction process (ORP) unit.

7. The process of claim 1, wherein the adsorbent is a binderless adsorbent comprising zeolite X having an average crystallite size of less than 1.8 microns.

8. The process of claim 7, wherein the adsorbent has at least 95% of its ion-exchangeable sites exchanged with barium or a combination of barium and potassium.

9. The process of claim 1, wherein the para-xylene separation unit is a simulated moving bed adsorption unit.

10. The process of claim 9, wherein the para-xylene separation unit uses a desorbent with a lower boiling point than the $C_8$ aromatic isomers.

* * * * *